(12) United States Patent
Homestad et al.

(10) Patent No.: US 6,191,262 B1
(45) Date of Patent: Feb. 20, 2001

(54) CONTRAST AGENT PREPARATION

(75) Inventors: Ole Homestad; Espen Myrbraten, both of Oslo (NO)

(73) Assignee: Nycomed Imaging As, Oslo (NO)

( * ) Notice: Under 35 U.S.C. 154(b), the term of this patent shall be extended for 0 days.

(21) Appl. No.: 09/419,290

(22) Filed: Oct. 15, 1999

Related U.S. Application Data

(63) Continuation of application No. PCT/GB98/01019, filed on Apr. 7, 1998
(60) Provisional application No. 60/044,409, filed on Apr. 29, 1997.

(30) Foreign Application Priority Data

Apr. 18, 1997 (GB) .................................... 9707880

(51) Int. Cl.$^7$ ...................................... C07F 13/00
(52) U.S. Cl. .................................. 534/16; 534/10; 534/13; 534/15; 423/263
(58) Field of Search ..................................... 534/7, 10–16; 424/1.11, 1.65, 9.1, 9.3, 9.4, 9.5; 423/263

(56) References Cited

U.S. PATENT DOCUMENTS

| | | | |
|---|---|---|---|
| 4,647,447 | 3/1987 | Gries et al. | 424/9 |
| 5,223,232 | * 6/1993 | Cuillerdier et al. | 423/9 |
| 5,662,874 | * 9/1997 | David | 423/263 |

* cited by examiner

*Primary Examiner*—Diana Dudash
*Assistant Examiner*—Dameron Jones
(74) *Attorney, Agent, or Firm*—Bacon & Thomas

(57) ABSTRACT

In the metallation of complexing agents such as DTPA-BMA with a lanthanide using a lanthanide oxide such as the lanthanide source, oxalic acid is used as a reaction accelerator.

13 Claims, No Drawings

CONTRAST AGENT PREPARATION

This application is a continuation of pending international application number PCT/GB98/01019 filed Apr. 7, 1998 (of which the entire disclosure of the pending, prior application is hereby incorporated by reference), which itself is a continuation of U.S. provisional application No. 60/044,409 filed Apr. 29, 1997, benefit of which is claimed under 35 USC 119(e).

This invention relates to a process for the metallation of complexing agents with lanthanides, e.g. gadolinium, and in particular to the preparation of lanthanide chelates such as those suitable for use as contrast agents in diagnostic imaging modalities such as magnetic resonance (MR) imaging.

In MR imaging, the use of lanthanide chelates as contrast agents has become well established. Several such agents (eg. Gd DTPA, Gd DTPA-BMA and Gd HP-DO3A, available under the trade marks Magnevist, Omniscan and Pro-Hance) are already commercially available, while still others are in early, middle and late stages of development. Such contrast agents are complexes of lanthanide ions with various different complexing agents (ligands) and a key stage of their production is the metallation of the ligand with a lanthanide. In general this is the last stage of primary production, ie. the production of the chemical drug substance that is subsequently formulated into the drug product in the secondary production phase.

Between metallation and secondary production the lanthanide complex must be thoroughly purified to remove unwanted impurities. As with any commercial drug synthesis, it is important to optimize yield of the desired product, reduce the levels of impurities produced during the various synthetic steps, and reduce process duration (and so. optimize the efficiency of reactor usage).

Metallation with lanthanides is normally performed by reacting the ligand with a lanthanide oxide (e.g. $Gd_2O_3$) in a heated aqueous medium. If this reaction takes too long, decomposition of the ligand can occur, resulting in reduction in yield and increased levels of impurities in the end product.

Thus for example in the metallation of DTPA-BMA (diethylene-triaminepentaacetic acid-N,N'-bis (methylamide) with gadolinium oxide, where the metallation proceeds too slowly some breakdown of the ligand to the mono-methylamide DTPA-MMA occurs. The reaction product then includes both Gd DTPA-BMA and a salt, eg. the sodium salt, of Gd DTPA-MMA. As a result NaGd DTPA-MMA must be removed by a recrystallization procedure.

The lanthanide oxide used in the metallation process is produced commercially by thermal decomposition of a lanthanide oxalate.

It has now surprisingly been found that the rate of the ligand metallation reaction is increased if the reaction medium includes oxalic acid or derivatives (eg. salts thereof).

Thus viewed from one aspect the invention provides a process for the preparation of a lanthanide complex by reaction of a lanthanide oxide with a complexing agent in an aqueous reaction medium, characterised in that oxalic acid or a salt or derivative thereof is used as a reaction accelerator.

When the ligand is subject to thermal decay, the process of the invention will represent an improvement in terms of speed of reaction as well as reduction in by-product formation; however, even where the ligand is thermally stable an improvement in speed of reaction will still be achieved.

The lanthanide used according to the invention may be any lanthanide but preferably is Eu, Th, Tm, Yb, Er or Ho, more preferably Dy, and most preferably Gd.

In this process where oxalic acid or a salt or derivative thereof is used as a reaction accelerator, this relates to further oxalic acid and not simply to the oxalate residue in the lanthanide oxide, even though this residue will of course contribute to the acceleration of the reaction.

The total amount of oxalic acid (or salt or derivative) added as a reaction accelerator is conveniently at least 10 μg oxalic acid/g $L_2O_3$ (where L is the lanthanide, e.g. Gd), preferably at least 50 μg/g, especially at least 100 μg/g, particularly at least 200 μg/g and more particularly at least 400 μg/g, eg. about 500 μg/g. The amount added will preferably be less than 2000 μg/g, particularly less than 1000 μg/g, preferably less than 800 μg/g.

The oxalic acid reaction accelerator can be added to the metallation reaction mixture as a separate reagent. However in alternative aspects of the invention some or all of the oxalic acid/oxalate may derive from oxalate impurity in the lanthanide oxide.

Thus viewed from a further aspect the invention provides a process for the preparation of a lanthanide complex by reaction of lanthanide oxide with a complexing agent in an aqueous reaction medium, characterised in that said process comprises the steps of: (a) determining the level of impurity in the lanthanide oxide; and (b) mixing lanthanide oxide from batches with different determined levels of impurity and/or including in the reaction medium a predetermined quantity of oxalic acid or a salt or derivative thereof; whereby by virtue of step (b) the reagents used in the metallation reaction contain oxalic acid (or salt or derivative) or oxalate at a total level of at least 50 μg oxalic acid per gram $L_2O_3$, preferably at least 100 μg/g, more preferably at least 200 μg/g, especially at least 250 μg/g and particularly preferably at least 400 μg/g, eg. up to 1750 μg/g, particularly 700 to 900 μg/g.

Viewed from a yet further aspect the invention provides a process for the preparation of a lanthanide complex by reaction of a lanthanide oxide with a complexing agent in an aqueous reaction medium, characterised in that for use as said lanthanide oxide is selected a lanthanide oxide having (eg. pre-analysed to contain) an oxalate impurity level of at least 100 μg oxalic acid/g lanthanide oxide, preferably at least 200 μg/, more preferably at least 250 μg/g, especially preferably at least 400 μg/g, more especially at least 700 μg/g.

The oxalate impurity level of the $L_2O_3$ may be inferred from its residue on ignition—the higher the residue the higher the oxalate content. Alternatively it can be determined by suitable analytical methods.

Where oxalic acid is added to the reaction medium, with or without predetermination of oxalate impurity levels of the lanthanide oxide, it may be added as a salt (eg. an alkali metal or alkaline earth metal salt), an ester or an amide or as the free acid. Lanthanide oxalates themselves may be used. However, preferably the free acids are used.

The use of oxalic acid (or salts or derivatives thereof) can reduce the metallation reaction time by a factor of two or more, eg. by a factor of up to 6.

The ligand which is metallated may be any ligand capable of producing a highly stable lanthanide complex, eg. one with a dissociation content of at least $10^{12}$. Preferably it will be a linear, cyclic or branched chelating agent, eg. a linear mono- or polychelant, a macrocyclic chelant or a branched polychelant (eg. a dendrimeric polychelant). Preferably the ligand will be a polyaminopolyoxyacid (eg. polyaminopolycarboxylic acid), such as one of the mono and polychelants suggested for lanthanide chelation in the patent literature relating to MR contrast agents, eg. the patent publications of Nycomed (including Nycomed Imaging and Nycomed Salutar), Sterling Winthrop, Schering, Bracco, Squibb, Mallinckrodt, Guerbet and Metasyn, eg. US-A-4647447, EP-A-71564, WO96/03154, WO96/01655, EP-A-430863, WO96/41830, and WO93/10824. Thus by way of example the ligand may be of formula

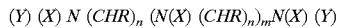

where m is 0, 1, 2, or 3; n is 2 or 3; y; each X is a hydrogen or a substituted $C_{1-6}$ alkyl group; each Y is a group X or the two Y groups together represent a $(CHR)_n$ bridge; and each R is hydrogen or a substituted $C_{1-6}$ alkyl group or a CHR-N(X)-CHR moiety may represent an optionally substituted, saturated or unsaturated 5 to 7 membered heterocyclic ring or a CHRCHR moiety may represent an optionally substituted, saturated or unsaturated 5 to 7 membered homo- or heterocyclic ring; where at least two X groups are alkyl groups substituted by sulphur, phosphorus or carbon oxyacid groups or amides or esters thereof, and where alkyl group substitution is preferably by oxyacid or oxyacid derivative groups, by hydroxyl groups, by optionally substituted phenyl groups, or by directly or indirectly attached polymer forming or biotargeting groups, eg. polyaminoacids, dendrimeric polymers, polyalkylene oxide groups, antibodies, antibody fragments, drugs, site specific peptidic groups (eg. oligopeptide binding motifs), etc.

Particular examples of appropriate ligands include DTPA, DTPA-BMA, DOTA, DO3A, HP-DO3A, BOPTA, PAMAM-polyDTPA, and PAMAM-polyDOTA. Especially preferred ligands include DTPA, DTPA-BMA, DOTA, and HP-DO3A.

The metallation reaction is preferably performed in aqueous solution, eg. in distilled water optionally containing a miscible cosolvent, at an elevated temperature, eg. 70° to 95° C., preferably 80°–90° C. During the reaction the pH is preferably 3 to 6. The pH may be controlled by addition of an acid or base, preferably an acid or base which produces pharmaceutically acceptable neutralisation products, such as hydrochloric acid and sodium hydroxide.

The progress of the metallation reaction will generally be monitored to determine the residual quantities of unreacted lanthanide oxide or ligand, with extra portions of oxide or ligand optionally being added until the reaction is deemed to be complete, eg. when a stable low concentration of ligand and negligible free lanthanide is detected. The reaction mixture will then be cooled, eg. to below 25° C. If necessary the pH of the reaction mixture is then adjusted, eg. about 6, for example using sodium hydroxide. The solution is then filtered and the lanthanide complex is isolated, eg. by crystallisation.

Using this procedure, the metallation reaction time for a ligand such as DTPA-BMA may be reduced from 2 to 3 hours to 1 hour or below, eg. 30 minutes.

Viewed from a further aspect the invention provides the use of oxalic acid (or a salt or derivative thereof) and/or a lanthanide oxide having a oxalate content of at least 100 µg oxalic acid/g lanthanide oxide, preferably at least 200 µg/g, as a reaction accelerator in the lanthanide metallation of a ligand.

The invention will now be described further with reference to the following non-limiting Examples.

EXAMPLE 1

A reactor vessel is charged with 180 mL of distilled water. After cooling to below 50° C., 43.2 g (119.17 mmoles) gadolinium oxide and 30.2 mg oxalic acid dihydrate are added. (The oxalic acid represents 500 ppm relative to the gadolinium oxide). During stirring, 100 g (238.42 mmoles) DTPA-BMA is added in one portion and the mixture is heated to 80°–90° C. After 0.5 hours, a sample of the reaction mixture is taken and analysed for the content of unreacted DTPA-BMA. If DTPA-BMA content is below 1% (w/v) a new sample is taken and analysed to confirm that the DTPA-BMA content is low and stable. If the DTPA-BMA content is above 1% w/v, the reaction mixture is stirred until sampling and analysis shows DTPA-BMA content to have stabilized below 1% w/w. (Optionally further DTPA-BMA or gadolinium oxide may be added to complete the reaction).

After complexation is complete, the reaction mixture is cooled to below 25° C. If necessary the pH is adjusted to about 6.1 to 6.4 by the addition of aqueous sodium hydroxide. The solution is filtered and GdDTPA-BMA is crystallized out.

EXAMPLE 2

An oxalate-contaminated batch of gadolinium oxide was analysed for oxalic acid content by titration with potassium permanganate in sulphuric acid. The content was found to be 270 µg oxalic acid per gram $Gd_2O_3$.

A sample of this batch was heated to 1100° C. for 2 hours to decompose the oxalate contamination.

Three metallation reactions were carried out using (i) heat treated contaminated gadolinium oxide, (ii) contaminated gadolinium oxide and (iii) contaminated gadolinium oxide with the further addition of 230 µg/g $Gd_2O_3$ of oxalic acid. The ligand was DTPA-BMA and the metallation reaction was carried out in aqueous solution at 80° C. The times required for the reactions to go to completion were respectively 2.5 hours, 1 hour and less than ½ hour.

What is claimed is:

1. A process for the preparation of a lanthanide complex by reaction of a lanthanide oxide with a complexing agent in an aqueous reaction medium, wherein oxalic acid or a salt thereof is used as a reaction accelerator.

2. A process as claimed in claim 1 wherein said lanthanide is gadolinium.

3. A process as claimed in claim 1 wherein oxalic acid is used as the reaction accelerator.

4. A process as claimed in claim 1 wherein 200 to 1000 µg oxalic acid/g lanthanide oxide are used as the reaction accelerator.

5. A process as claimed in claim 1 for the preparation of a lanthanide complex by reaction of a lanthanide oxide with a complexing agent in an aqueous reaction medium, wherein said process comprises the steps of: (a) determining the level of impurity in the lanthanide oxide; and (b) mixing a lanthanide oxide from batches with different determined levels of impurity and/or including in the reaction medium a predetermined quantity of oxalic acid or a salt thereof; wherein in step (b) the reagents used in the metallation reaction contain oxalic acid (or salt) or oxalate at a total level of at least 50 µg oxalic acid per gram lanthanide oxide.

6. A process as claimed in claim 1 wherein said lanthanide is gadolinium.

7. A process as claimed in claim 1 wherein a predetermined amount of oxalic acid or a salt thereof is included in the reaction medium.

8. A process as claimed in claim 1 wherein a predetermined amount of oxalic acid is included in the reaction medium.

9. A process as claimed in claim 1 for the preparation of a lanthanide complex by reaction of a lanthanide oxide with a complexing agent in an aqueous reaction medium, wherein said lanthanide oxide is a lanthanide oxide having an oxalate impurity level of at least 100 μg oxalic acid/g lanthanide oxide.

10. A process as claimed in claim 1 wherein said lanthanide is gadolinium.

11. A process as claimed in claim 1 wherein said complexing agent is a polyaminopolycarboxylic acid.

12. A process as claimed in claim 1 wherein said complexing agent is selected from DTPA, DTPA-BMA and HP-DO3A.

13. A process as claimed in claim 1 wherein said complexing agent is DTPA-BMA.

* * * * *